United States Patent [19]
Sielaff et al.

[11] 3,983,864
[45] Oct. 5, 1976

[54] METHOD AND APPARATUS FOR IN VIVO BLOOD GAS ANALYSIS

[75] Inventors: Ulrich Sielaff, McFarland; Wilfried R. Peickert; Dale A. Brinkman, both of Madison, all of Wis.

[73] Assignee: Airco, Inc., Montvale, N.J.

[22] Filed: July 7, 1975

[21] Appl. No.: 593,606

Related U.S. Application Data

[63] Continuation of Ser. No. 493,938, Aug. 1, 1974, abandoned.

[52] U.S. Cl. .................. 128/2 G; 23/230 B; 23/232 C; 73/421.5 R; 128/2 F; 128/2 L; 128/214.4
[51] Int. Cl.²................................
[58] Field of Search .......... 128/2 G, L, F, E, 214.4, 128/348; 421.5 R;23 R;23.1/; 23/230 B, 232 C

[56] References Cited
UNITED STATES PATENTS

| | | | |
|---|---|---|---|
| 3,512,517 | 5/1970 | Kadish et al. ................ | 128/2 E |
| 3,572,315 | 3/1971 | Cullen II ...................... | 128/2 E |
| 3,585,002 | 6/1971 | Boys............................. | 23/232 C |
| 3,640,269 | 2/1972 | Delgado........................ | 128/348 |
| 3,649,199 | 3/1972 | Littlejohn...................... | 23/230 B |

OTHER PUBLICATIONS
Med and Biol. Engng., vol. 8, No. 2, pp. 111–128, (1970).
Journ, of Thoracic and Cardiovascular Surg., vol. 62, No. 6, Dec. 1971, pp. 844–850.

Primary Examiner—Kyle L. Howell
Attorney, Agent, or Firm—Roger M. Rathbun; Edmund W. Bopp; H. Hume Mathews

[57] ABSTRACT

Method and apparatus for withdrawing and analyzing gases dissolved in liquid, more specifically, equilibrated blood gas samples in vivo. A catheter including a semipermeable membrane, connected to include a volume of carrier gas at atmospheric pressure, is introduced percutaneousluy into the bloodstream. After a predetermined period, equilibratin occurs between the blood gases and the carrier gas. By means of displacement in the volume or reduction in the pressure, the carrier gas including the equilibrated gas is then removed from the semipermeable membrane to another area for analysis. A corresponding volume of carrier gas is replaced in the semipermeable membrane from an inlet supply.

25 Claims, 6 Drawing Figures

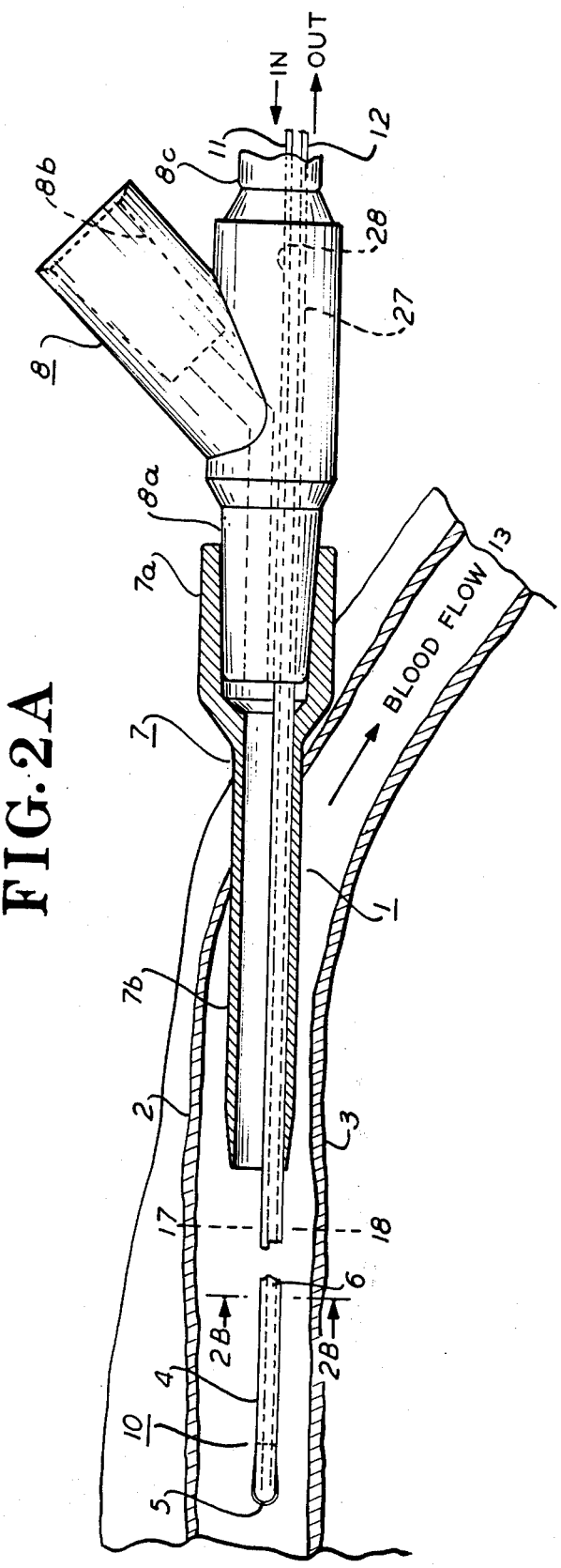
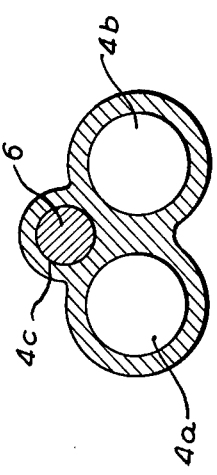

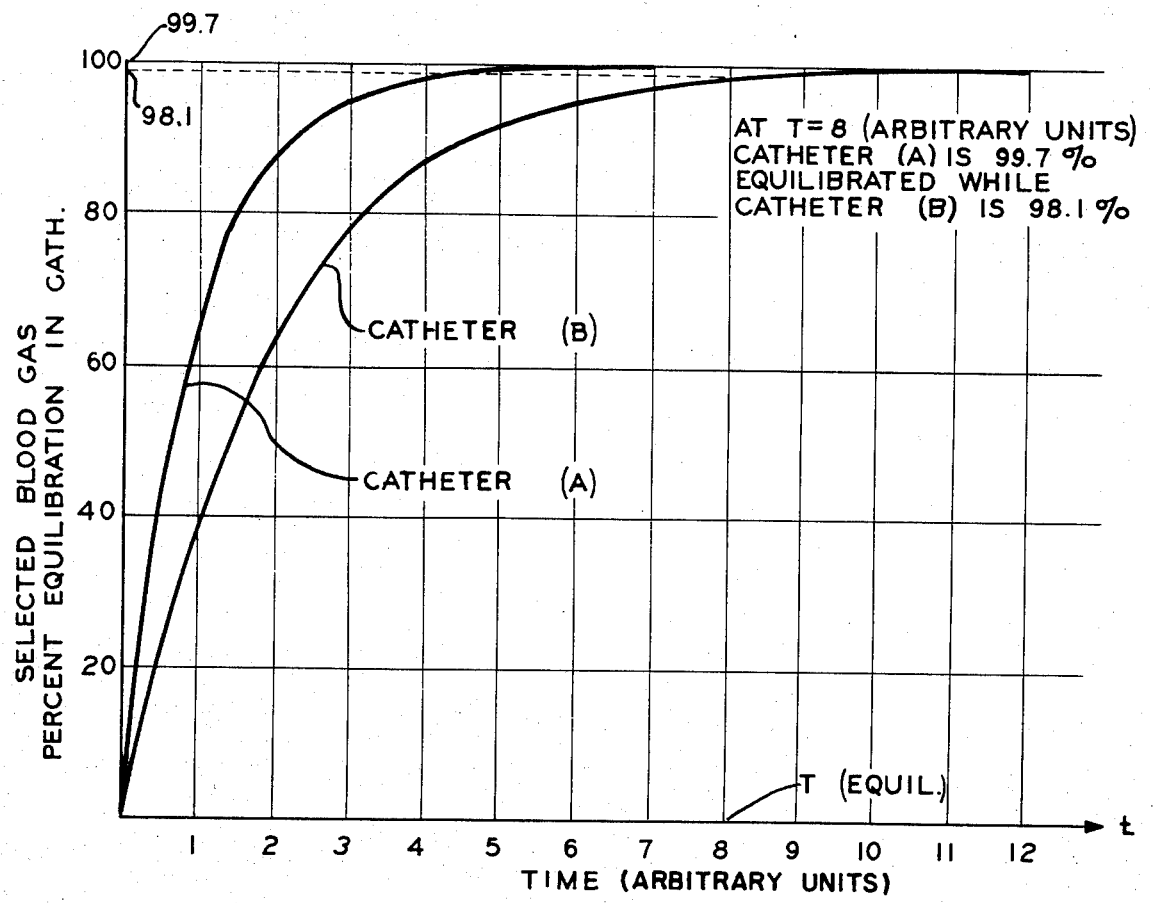
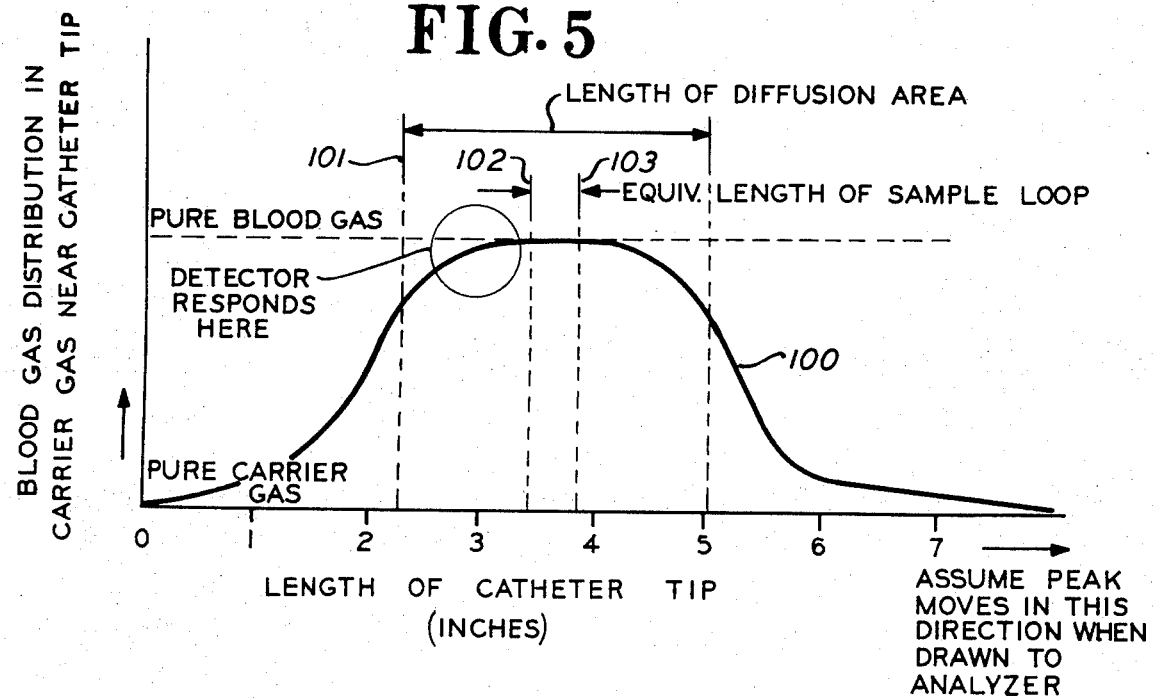

METHOD AND APPARATUS FOR IN VIVO BLOOD GAS ANALYSIS

This is a Continuation of application Ser. No. 493,938, filed Aug. 1, 1974, now abandoned.

BACKGROUND OF THE INVENTION

The present invention relates to the sampling and analysis of gases dissolved in liquid, and more specifically to the vivo analysis of gases dissolved in the blood.

Blood gases have been detected and measured in vivo by a variety of electronic means. The most successful have been variations of the polarographic electrode for oxygen and modified pH electrodes for carbon dioxide. Oxygen, $CO_2$ and other dissolved blood gases have also been detected and measured in the prior art on the basis of their flow rates into an evacuated gas permeable membrane tipped catheter in contact with the blood. The prior art systems of the latter type are specifically designed to operate with mass spectrometers. Blood gases pass through a small membrane area and are drawn to the mass spectrometer at a rate proportional to their partial pressures in the blood. The mass spectrometer determines the relative number of each type of gas molecule passing into the system and thus, with proper calibration, the partial pressures in the blood may be indirectly determined.

All of the prior art methods described here rely on the rate of gas diffusion through a membrane to indicate the partial pressures of the gases in the blood. In such measurements, a steady state diffusion rate is reached which is a function of the membrane thickness, the membrane surface conditions, blood velocity, temperature, etc., which parameters are either unknown or difficult to control. The combined effects of these variables on the overall measuring system can only be overcome by calibrating each system after it is in place in the artery. It is also known that these variables may change during the time that a continuous blood gas measurement is being made. The membrane probes are known to change position within the blood stream resulting in varied blood flow conditions which can alter the gas diffusion rates. The membrane characteristics will also change under the effect of protein buildup on their surfaces, thus changing the diffusion rates. It is thus necessary to calibrate such systems frequently during their use to account for the changes in gas diffusion rates which naturally occur. Each calibration necessitates the extraction of a blood sample for gas pressure determination with an in vitro instrument.

BRIEF DESCRIPTION OF THE INVENTION

Accordingly, it is the principal object of the present invention to provide for the in vivo sampling of blood gas by a partial pressure technique which will yield measurements that are more reliable and accurate than prior art techniques. A more specific object is to provide a partial pressure blood sampling technique which provides a gas sample of sufficient volume to be accordingly adapted for analysis by a gas chromatograph or any other instrument designed to analyze small gas volumes. Another object of the invention is to provide a system of the foregoing type, in which the necessity for calibration is substantially reduced. A further object of the invention is to provide for partial pressure sampling of blood gases at substantially atmospheric pressure.

These and other objects are realized, in accordance with the present invention, in a method and apparatus for intermittently sampling the gases dissolved in the blood in vivo, employing a catheter in the form of a highly diffusible double lumen tubular membrane which is introduced into the bloodstream. Carrier gas from an inlet supply source is introduced into the membrane at about atmospheric pressure and allowed to equilibrate for a predetermined time with the blood gases passing through the diffusible membrane. The equilibrated gas is then moved to another section of the system where a portion of it is removed for subsequent analysis. The equilibrated gases are transported into an analyzer which preferably takes the form of a gas chromatograph. This is accomplished by a vacuum means which moves the equilibrated gas sample from the equilibration region to a sampling valve.

A carrier gas suitable for the present invention is characterized by either slow rate of diffusion through the selected membrane or low solubility in blood, or both, relative to the gases to be measured. Since the diffusion area in the catheter comprises a long, narrow tube, complete equilibration is only achieved in the central section. Carrier gas diffusion into the blood gas produces a "bell shaped" distribution of the diffusing blood gases relative to the carrier gas.

In accordance with a preferred embodiment of the invention, a thermal conductivity sensor is interposed into the system to detect the presence of the equilibrated gas sample just before it moves into the sampling valve section of the system. For this embodiment, a pump is used at negative pressure to move the gas to the sampling region. The pump operates upon the opening of a valve in the conduit system to draw the equilibrated volume of gas along the connecting conduit. The thermal conductivity detector is calibrated to detect passage of the blood gas peak, in response to which it generates a signal which switches a sampling valve, causing it to direct a small preselected volume of gas into the gas analyzer. A continuous flow of gas is simultaneously admitted from an auxiliary carrier source which serves to drive the equilibrated gas sample into the analyzer.

In accordance with another feature, the valve at the output terminal of the catheter is connected to perform a selector function between the diffusion area, the sampling valve and a calibration source. When this valve is closed to the catheter terminal, it may serve to supply a flow of calibrating gas to the sampling valve and gas analyzer for calibration purposes.

For the purposes of the embodiment including the thermal conductivity sensor, the carrier gas should have a significantly different thermal conductivity than any of the gases being measured in the blood. Helium, for example, allows a blood gas mixture containing $O_2$, $CO_2$, $N_2O$, $N_2$ or anesthetic vapors to be easily detected by the thermal conductivity detector adjacent to the sampling valve.

A particular advantage of the techniques and apparatus of the present invention over prior art systems for in vivo measurement of dissolved blood gases is that a gas sample of substantially the same partial pressure as in the blood is made available for analysis. The system of the present invention operates safely since carrier gas is transported at substantially below atmospheric pressure. Moreover, it provides a relatively large volume of blood gases and is accordingly well adapted for use with the gas chromatograph type of analyzer, which is simpler and more economical than the mass spectrometer previously used in combination with prior art systems employing diffusible membranes. Further advantages of the system of the present invention are that it requires less calibration than systems of the prior art; and its operation is not sensitive to changes in body temperature.

These and other objects, features and advantages will be apparent to those skilled in the art after a detailed study of the specification hereinafter with reference to the attached drawings.

SHORT DESCRIPTION OF THE DRAWING

FIGS. 2A and 2B are respectively a longitudinal section and an enlarged cross-section of a catheter configuration suitable for the purposes of the present invention shown in place in a bloodstream.

FIG. 3 is a plot against time of the percent of equilibration of a selected blood gas in two selected catheter tips during equilibration.

FIG. 5 shows a graphical representation of the distribution of blood gases in a carrier gas along the length of the catheter tip.

DETAILED DESCRIPTION OF THE INVENTION

Figure 1:
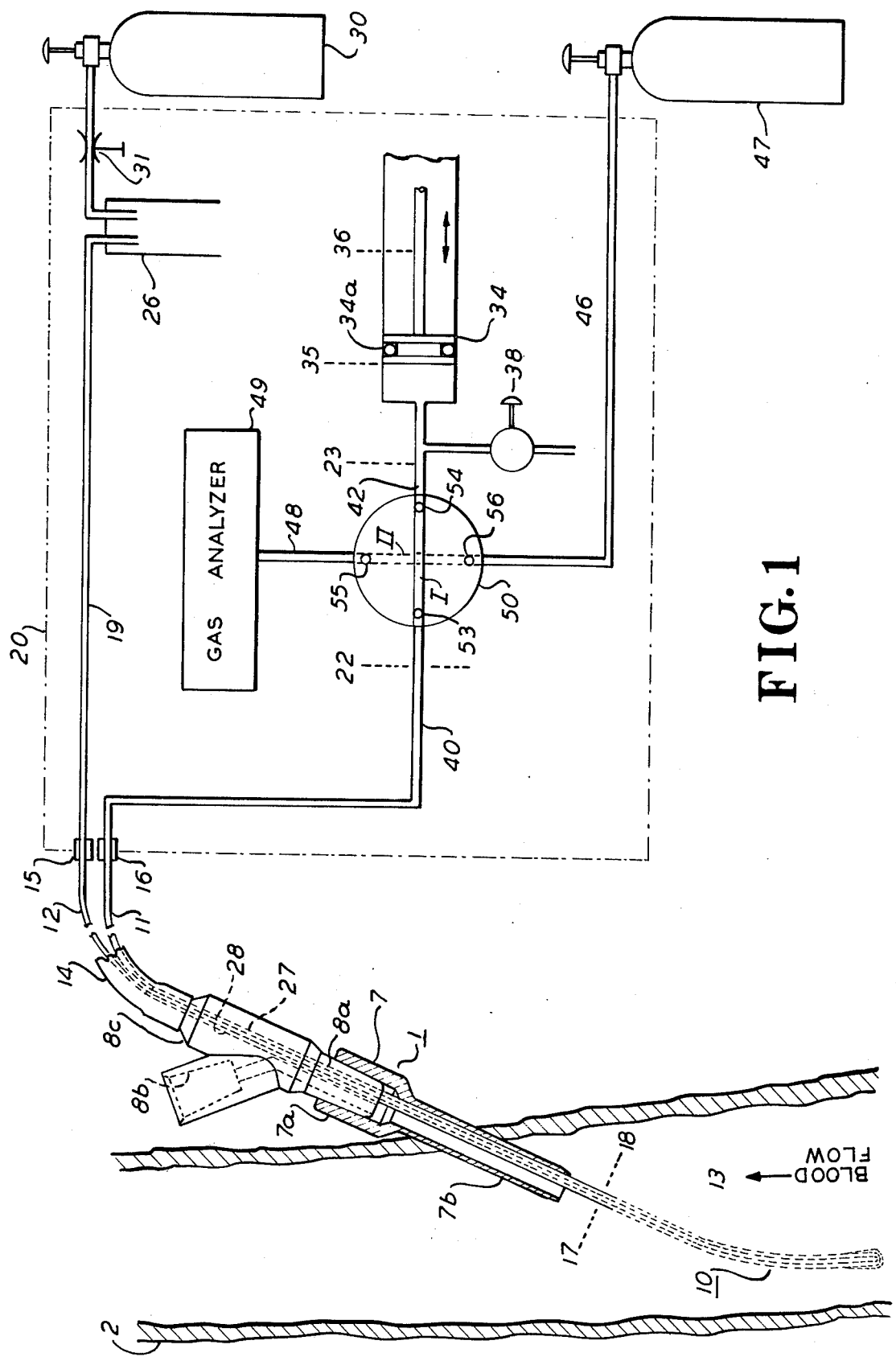
FIG. 1 is a schematic diagram of the simplest embodiment of a conduit system in accordance with the present invention operated by a displacement volume means, including a diffusible membrane catheter in place in the bloodstream of a subject for measuring dissolved blood gases.

The simplest embodiment of the invention is represented schematically in FIG. 1. While, for clarity, the components in FIG. 1 are depicted in a configuration which requires manual operation, it is evident that by application of electronic logic circuitry, well known in the state of the art, the system can be made to operate entirely automatically.

Basic to the operation of this system is a suitable catheter 1 which can be inserted through the skin into a blood vessel. A preferred form for this purpose is disclosed in the companion application Ser. No. 493,939 filed Aug. 1, 1974 by U. Sielaff and W. Peickert, now abandoned, and application Ser. No. 611,473, a Continuation-in-Part thereof, filed Sept. 8, 1975, that part of the disclosure of which as originally filed being made a part hereof by reference. The general feature of this design is represented in simplified form in longitudinal section 2A and enlarged cross-sectional view in FIG. 2B. The design is discussed in greater detail in the application of Sielaff and Peickert, supra. It will be understood that such a catheter may have a variety of geometries, but must have an inlet and outlet port which communicate to a tubular membrane area. A continuous path for gas flow must be available between an inlet terminal and outlet terminal, both outside of the body (See FIG. 1). The proximal portion of the catheter 1, outside of the body, is preferably constructed of a pair of non- or low gas permeable tubes 11, 12 of, for example, stainless steel, each from 4 to 6 feet in length, respectively, about 0.013 and 0.022 inch in inner diameter, which carry gas to and from the distal catheter tip region 10 within the body.

Connecting tubes 11 and 12 are jacketed in a covering tube 14 of polyvinylchloride or the like, of sufficient length to reach conveniently from a patient measuring site to an instrument, the components for which are schematically within the dotted line 20 (FIG. 1).

Referring to FIGS. 2A and 2B and a highly gas permeable tubular membrane 4 of, for example, a silicone polymer or similar non-toxic highly permeable membrane material, is interposed into the bloodstream of a living subject through cannula 7. The membrane is more particularly described in the companion application of U. Sielaff and W. Peickert, supra. The cannula is of a conventional commercially available type having hub 7a and a distal end comprising a plastic tube 7b. The latter accommodates the proximal end of membrane 4 coaxially guiding it into place in vessel 2, where it may be retained semi-permanently, even when the plug to measuring system 20 is disconnected.

The cross-sectional geometry of the membrane 4 may be varied; but to expose maximum surface area of the membrane in the blood vessel, a tri-lumen membrane construction is chosen in the embodiment as shown in the cross-sectional view FIG. 2B. The two larger lumens 4a, 4b are each about 0.011 inch in diameter and are connected by means of a U-shaped stainless steel or nickel tube 5, thus permitting a reversal in the direction of gas flow from one lumen to the second lumen. The small 0.006 inch diameter lumen 4c accommodates a stainless steel wire 6 of 0.006 inch diameter which is soldered at its distal end in a smooth joint to the inner curve of the stainless steel U-shaped tube 5. The wire 6 serves the purpose of providing proper rigidity to the membrane 4 in the longitudinal direction, permitting it to be more readily inserted through the cannula 7. The wall thickness of the membrane 4 is preferably, for example, 0.002 inch to assure good gas diffusibility and still provide adequate catheter lumen rigidity. A membrane exposed length of 5 inches beyond the end of the tubular portion 7b of cannula 7 provides a combined lumen volume of 16 microliters for gas diffusion. It will be understood that in substitution for the disclosed U-shaped tube 5, alternative devices can be employed in order to pass gas between the ends of lumens 4a and 4b, such as for example, piercing one or more holes in the webbing between the two.

At their proximal ends the lumens 4a, 4b respectively accommodate a pair of metal connector tubes 27, 28 which pass through a bore along the axis of the shank 8a and one arm 8c, of a Y-shaped adapter plug 8, which may, for example, be molded from acetal plastic or the like. The tubes 27, 28, which extend from the end of shank 8a to about ⅛ inch beyond the end of arm 8c are press-fit into the axial bore, and sealed into position by, for example, a silicone adhesive. The male connector 8a of the adapter 8, and the other branch 8b, comprising a female connector are of a form known in the art as a "Luer taper". The male Luer taper 8a provides a quick leak-proof connection to the hub 7a of cannula 7. The female Luer taper 8b communicates via a separate passage with the blood surrounding the membrane portion 4 inside the cannula 7, thus providing a port for taking blood samples without disturbing the catheter.

The connecting tubes 27, 28 are joined beyond the end of adapter branch 8c to the respective tubular members 11, 12 which are of a substantially non-diffusible material for gases, such as, for example, stainless steel.

tubes 11 and 12 in the insulating tubular jacket 14 extend 5 or 6 l feet beyond the end of adapter 8 terminating in a receptacle and plug which leads into the blood gas analysis system 20 through down gas terminal 15 from the carrier gas source 30 and return gas terminal 16 to the chromatograph analyzer, as will be explained. Additional features of the catheter are described in more detail in the companion application of Sielaff and Peickert, supra, incorporated by reference.

Referring to FIG. 1, the system's operation may be described as follows: A suitable carrier gas supplied from a conventional gas supply cylinder 30, which may be pressurized for convenience of transport and storage, is metered through a conventional restricting valve 31 to a chamber 26 which is open to atmosphere. As previously pointed out, the supply gas in the present embodiment is helium, although it will be understood that alternatively it can be any gas characterized by slow diffusion or low solubility, or both, relative to the gases to be measured. The flow into chamber 26 is regulated such that all of the ambient air is expelled from within, and only pure carrier gas surrounds the inlet of tubing 19, which leads from the instrument to the catheter inlet port 15.

The conduits of the system are preferably of stainless steel, or other non-diffusible material having an inner diameter of, say 0.013 inch in the present example. Tubing 19 extends into the inlet of catheter 1, through connecting tube 12, through diffusing loop 10, back to the measuring portion of the instrument 20 through non-diffusible tubes 11 and 40 and through sampling valve 50 to a volume displacement means 34. The pump 34 may take the form of a conventional syringe having a total volume displacement of approximately 200 microliters between evacuation and exhaust positions. As the piston 34a in volume displacement means 34 is moved from evacuation position 35 to exhaust position 36, a reduction of pressure therein causes a volume of carrier gas equal to the pump's displacement to move through the system.

Interposed between conduits 40 and 42 is a sampling valve 50 with a known specific internal volume between its ports 53 and 54. This may take the form of any standard internal sample loop chromatographic sampling valve, well known in the art. In the present embodiment, the preselected volume between ports 53 and 54 is, say, one microliter. The volume of sampling valve 50 between ports 53 and 54 should preferably be chosen so that the diffusion volume in the catheter tip 10 extending between 17 and 18 is at least about ten times the volume enclosed between ports 53 and 54 in sampling valve 50. This assures that a fully equilibrated portion of sample gas is injected into gas analyzer 49. The internal path of sampling valve 50 should have approximately the same bore as the connecting tubing 40 to minimize gas mixing.

In position I of valve 50, shown in FIG. 1, gas is free to flow from chamber 26 through catheter 1 and ports 53 and 54 to the volume displacement pump 34. A second bore between 56 and 55 connects another gas supply source 47 to a gas analyzer 49, which is flowing continuously. Additionally, a vent valve 38 is interposed in conduit 42 which may be opened to expell carrier gas to atmosphere when the volume displacement pump 34 is returned to position 35.

When sampling valve 50 is rotated through 90° to take position II, the gas in the tube between 53 and 54 is injected into the conduit between 56–55, and the dotted channel replaces the original channel moving to the catheter line.

In the present embodiment the gas analyzer may take the form of a gas chromatograph of a micro chromatographic type adapted for the measurement of small volume gas samples of one microliter or less.

The equilibration and sampling process will operate as follows. Assuming an initial condition of pure carrier gas throughout the entire system at time zero, gases within the blood 13 in contact with the permeable tubular membrane 4 diffuse inwardly at rates dependent on the membrane permeability, diffusion area and thickness of the membrane, and the respective partial pressure gradients. At the same time carrier gas may diffuse out of the catheter into the blood 13.

The equilibration process is indicated graphically in FIG. 3 which shows two equilibration curves A and B which may either represent the conditions of two different catheters, or may represent the rate of equilibration of the same catheter under different conditions within the body. The significance of choosing a sufficiently long equilibration time T is demonstrated by these two curves. Since both are essentially exponential functions, it can be seen that, if the equilibration time is picked long enough, variations in the specific catheter and its diffusing properties, blood flow, or temperature will have very little effect on the final equilibrated partial pressure level. Although this technique sacrifices strictly continuous readout of the blood gas values, if one allows this equilibration to go on for approximately two minute intervals, it results in more reliable and accurate measurements than prior in vivo blood gas measuring systems. An interval of approximately two minutes is a sufficient time to permit a gas depleted area near the catheter to become replenished, such that the sample volume is completely equilibrated with blood gases at the same conditions as they exist in the blood.

After an appropriate equilibration time, assuming the components to be in the positions shown in FIG. 1 with the on-off valve 38 closed, the piston is now moved to position 36, which displaces the gas volume within the system, such that the gas at point 18 moves to point 23 and the gas at point 17 moves to point 22. The distribution of blood gas equilibrated within the membrane tip is shown in FIG. 5. It is evident that the most complete equilibration is achieved midway between points 17 and 18; and for the most accurate operation, the displacement volume must be picked so that the center of the equilibration region is drawn exactly to the center of the sample valve 50. During the gas drawing phase, the system undergoes a slight negative pressure condition (of the order of −10 cm. of water), which is allowed to return to atmospheric pressure as carrier gas is replenished from chamber 26. After the gas has been drawn to position 22–23 with sampling valve 50 in position I, and the pressure is allowed to return to atmospheric throughout the entire system, sampling valve 50 is rotated ninety degrees, which places the ports containing the blood gases, into position II between points 55 and 56 connecting conduits 46 and 48. Helium from auxiliary supply 47 then flows through conduit 46 and into valve 50 to inject this known volume of blood gas mixture into the gas analyzer 49 for subsequent analysis. Valve 38 in output conduit 42 is then opened to atmosphere, the piston 34a of pump 34 is returned to position 35, and the system is purged of gas in preparation for the next drawing cycle. Valve 50 is quickly returned to its original position I between conduits 40 and 42 in preparation for the next sample arrival.

The following table summarizes the sequence of operations of the embodiment of FIG. 1:

TABLE I

| Steps | Time | Operation |
|---|---|---|
| 1 | 2 min. | With valve 38 closed, catheter tip 10 equilibrates with blood gases. |
| 2 | 10 sec. | Valve 50 in position I; sample drawn from tip of catheter 1 into sampling valve 50 as piston 34a moves from 35 to 36. |
| 3 | 1 sec. | Valve 50 is switched from position I to position II to inject sample into gas analyzer 49. |
| 4 | 2 sec. | Exhaust valve 38 opens; and piston 34a moves from 36 to 35 to purge cylinder 34. |
| 5 | (Beginning of 1) | Vent valve 38 closes in preparation for next draw. (Process is repeated). |

An important feature of this system is that the blood gases, once equilibrated within the catheter tip inside the body, are moved to an analysis section, and there, before they are injected into the analyzer 49, are allowed to come to the same total pressure as they occupied within the body. This greatly simplifies the calibration process, which is based on the assumption of complete equilibration in the body.

Figure 4:
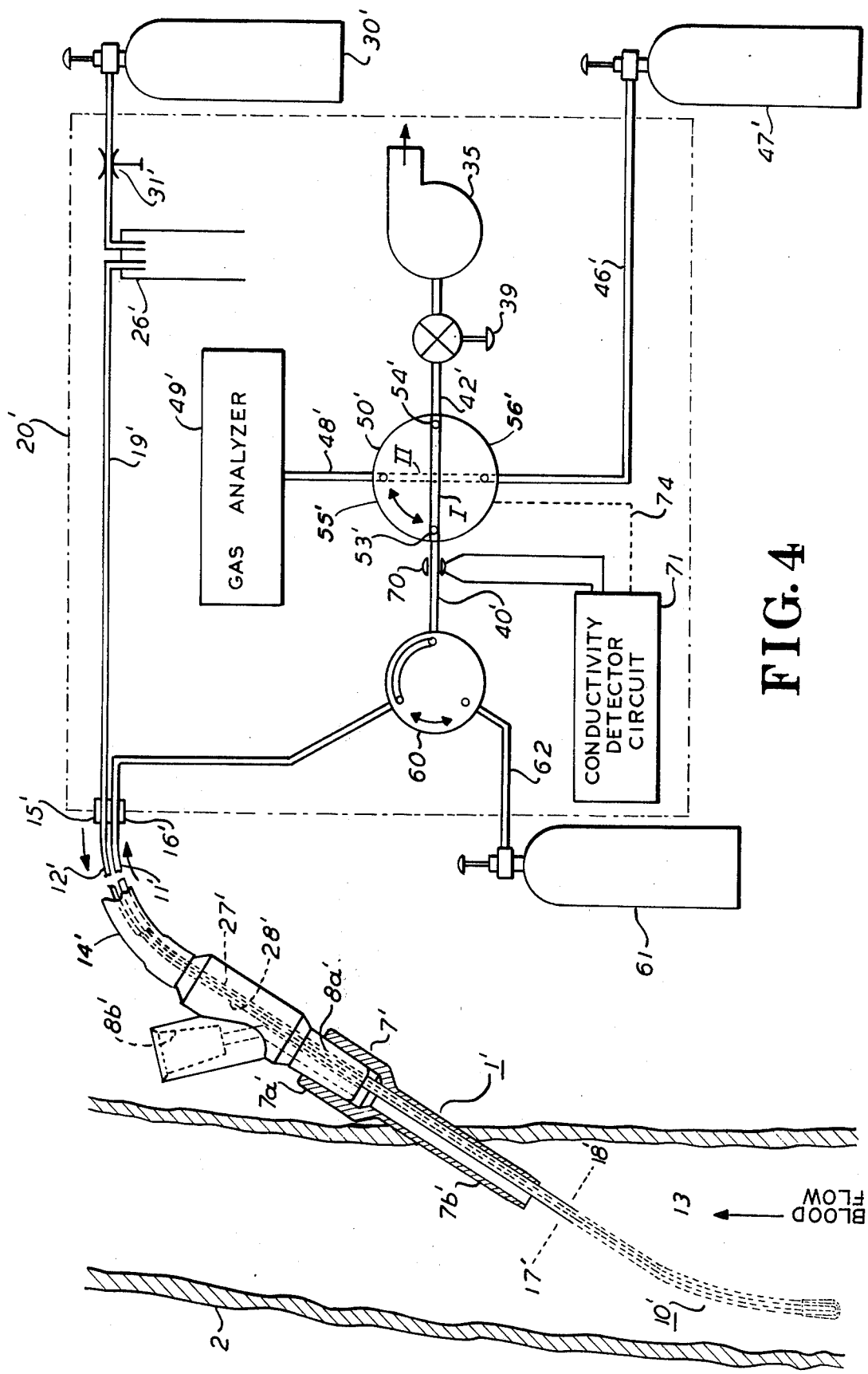
FIG. 4 is a schematic diagram of a modification of the system of FIG. 1, including thermal detecting means for automatically operating the valve in the sampling area, including a vacuum pump which replaces the displacement volume means of FIG. 1.

FIG. 4 shows a modified form of the invention in which the displacement pump 34 of FIG. 1 is replaced with a continuous vacuum source 35. This system includes, in addition to the components disclosed with reference to FIG. 1 of the drawings, a source 61 of calibrating gas which may be connected by conduit 62 through three-way valve 60, to tube 40'. In FIG. 4 the primed numbers represent components which are substantially similar to their like numbered components described with reference to FIG. 1, and will not be redescribed.

The vacuum source 35, which can be controlled by an on-off valve 39 in conduit 42', is preferably pumping means of a low power vibrating type, substantially of a diaphragm form conventionally used in ornamental fish tanks. Upon opening of valve 39 to conduit 42', source 35 operates to produce a negative pressure of 10–20 centimeters of water in conduit 42', thereby drawing through valve 50' equilibrated gas from the catheter tip 10'.

The principal difference between the present embodiment and that of FIG. 1 is the use of the thermal detector circuit 70, 71, the operation of which will be presently explained.

As previously pointed out with reference to FIG. 1, the diffusion area in catheter 1' is a long narrow tube. Substantially complete equilibration between the blood gas and the carrier gas is achieved in only the central section of the diffusion area, between the points 17' and 18'. If the distribution along the tube of the diffused gases in the carrier gas were plotted, a "bell" shaped curve 100 would result which is substantially flat in the center of the equilibration loop (See FIG. 5). When vacuum source 35 operates, upon the opening of valve 39, the volume of equilibrated gas which moves along conduit 40' to the sample valve 50' has a clearly detectable maximum variation of thermal conductivity. As indicated in FIG. 5, it is desirable that the volume of equilibrated gas is drawn to such a position with reference to valve 50' that the degree of equilibration is substantially uniform between ports 53' and 54'. Thus, the volume sampled would represent the flat mid-position of curve 100, between points 102 and 103. For the purposes of this embodiment, helium is preferred for a carrier gas because its thermal conductivity differs substantially from that of any of the blood gases to be measured.

The detector element 70 preferably comprises a hot wire type well known in the art, such as those used for chromatographic analysis, or other thermally sensitive element, which is interposed into conduit 40' in a position closely adjacent the input end of the sampling valve 50'. Because of the physical size of the conduit 40' into which this is interposed, it is necessarily very small.

The thermally sensitive element 70 responds electrically to the peak of the equilibrated gas, passing a signal to detector circuit 71. Sensitive element 70 is interposed into pipe 40', close to the sampling valve 50', preferably to coincide with a position represented by the area between dotted line 101 and 102 of diffusion curve 100 of FIG. 5, so that element 71 responds to the space rate of increase in thermal conductivity of the gas mixture, just past the peak as represented by the positive slope of curve 100. The received signal in detector circuit 71 actuates an associated electrical system indicated by the dotted lines 74 for operating the sampling valve 50' to move the sample loop into the analyzer circuit.

A particular advantage of the thermal detector embodiment of FIG. 4 is that it works substantially better than the system disclosed in FIG. 1, because of the great precision required for the draw into the sampling valve.

The auxiliary carrier gas from source 47' drives the gas in sample valve 50' through conduit 48' and into the gas analyzer 49', as in the previous embodiment. The electronic means indicated by dotted lines 74 are well known in the art and could comprise, for example, solenoid controls to rotate valve 50' to the desired positions.

A further modification of the circuit of FIG. 4 includes means for calibrating the operation of the system. This includes a source 61 of calibration gas which is connected through a conduit 62 to valve 60, which leads into the conduit 40'. The valve 60 may be a three-way valve, so designed that the terminal of catheter 1' can be closed off while conduit 62 is open to conduit 40'. The calibration gas, which is preferably a mixture of similar composition as the blood gases, flows continuously during the calibration cycle, and is injected into the gas analyzer 49' through sampling valve 50'.

It will be understood that although the present invention has been disclosed with reference to specific embodiments for the purposes of illustration, it is not limited to the specific forms or components shown and described, but is only limited by the scope of the appended claims.

We claim:

1. A method of sampling gases dissolved in a liquid comprising the steps of:
   introducing a catheter into the liquid, at least a portion of said catheter comprising a membrane being permeable to said gases but substantially impermeable to said liquid, said permeable portion directly contacting said liquid;
   admitting carrier gas at about atmospheric pressure into said catheter to contact said membrane;
   permitting said carrier gas to equilibrate with the gases dissolved in said liquid whereby said dissolved gases pass into said catheter through said membrane and are mixed with said carrier gas; and
   removing at least a portion of said mixed gases from said catheter.

2. A method of intermittently sampling and subsequently analyzing gases dissolved in the bloodstream of a living organism comprising the steps of:
   introducing a member comprising a semipermeable membrane into said bloodstream, said membrane being permeable to gases but substantially impermeable to blood;
   admitting carrier gas at about atmospheric pressure into said semipermeable membrane member within the bloodstream;
   allowing equilibration between a volume of said carrier gas and said dissolved blood gases through the lateral walls of said semipermeable membrane member for a predetermined time;
   removing at least a portion of said volume of carrier gas containing said equilibrated blood gases from said semipermeable membrane member; and
   isolating and analyzing said removed equilibrated gases in said portion of carrier gas.

3. A method in accordance with claim 2 wherein said carrier gas is characterized relative to said dissolved blood gases by either a slow rate of diffusion through said membrane or a low solubility in blood, or both.

4. The method in accordance with claim 2 wherein said volume of carrier gas containing said equilibrated blood gases substantially exceeds the portion analyzed.

5. The method in accordance with claim 4 wherein said volume of carrier gas including said equilibrated blood gas exceeds the portion analyzed by at least a factor of ten.

6. The method is accordance with claim 2 in which the steps of removing and isolating a portion of the volume of said carrier gas containing said equilibrated gases from the remaining carrier gas is carried out by first reducing the pressure in means connected to said membrane member for sampling a discrete portion of said volume, thereby causing the said portion to move from said member to said sampling means, connecting said sampling means to a gas analyzer and subsequently forcing the said portion containing said equilibrated gases from said sampling means to said gas analyzer by introducing into said sampling means carrier gas from an auxilliary source.

7. The method in accordance with claim 6 which comprises the steps of detecting the peak amount of said equilibrated gas distributed in said portion of carrier gas as said portion moves from the membrane member to said sampling means, and actuating valve means to admit a discreet amount of said portion including said equilibrated gases to said gas analyzer when said peak is positioned in said sampling means in a preselected position in relation to the intake of said gas analyzer.

8. The method in accordance with claim 7 wherein said peak generates a signal, detecting and utilizing said signal to actuate said valve means.

9. The method in accordance with claim 7 wherein said carrier gas is characterized by a thermal conductivity which is substantially different from that of the blood gas to be measured.

10. The method in accordance with claim 9 wherein helium is employed as a carrier gas.

11. The method in accordance with claim 9 wherein the space rate of change to thermal conductivity in said portion of carrier gas including said equilibrated blood gases is represented by a "bell shaped" curve, detecting a signal corresponding to the space rate of change in said thermal conductivity represented by the change in slope of said curve, and utilizing said signal to actuate said valve means to receive said portion including said equilibrated blood gases at a position represented by the flat top portion of said curve.

12. A device for the sampling of gases dissolved in liquid characterized by a catheter, a portion of which comprises a membrane permeable to gas diffusion but substantially impermeable to diffusion by said liquid, said catheter being designed for introduction into the liquid to be analyzed, a carrier gas source connected to the gas permeable membrane portion of said catheter comprising means to supply carrier gas thereto at substantially atmospheric pressure, said supply means being adapted to retain a volume of carrier gas contacting the gas-permeable membrane portion for a preselected period of time to permit the establishment of an equilibrium between the carrier gas and said dissolved gases causing mixing thereof within the catheter, and means connected to the catheter to remove therefrom at least a portion of the carrier gas including the mixed equilibrated gases.

13. A system for intermittently sampling and subsequently analyzing gases dissolved in the blood which comprises in combination:
   a catheter comprising intake and exhaust terminals at its proximal end connected by a continuous passage formed in a semipermeable membrane member constructed for insertion at the distal end of said catheter into the bloodstream of a subject to be analyzed, said membrane being permeable to gases but substantially impermeable to blood;
   a source of carrier gas connected to the intake terminal of said catheter and comprising means for supplying carrier gas to the passage formed in said membrane member at about atmospheric pressure;
   means for retaining a volume of said carrier gas in said passage for a preselected interval to allow equilibration between said carrier gas and said dissolved blood gases;
   means connected to the exhaust terminal of said catheter for removing said volume of carrier gas including said equilibrated blood gases from said passage;
   means connected to said last-named means for analyzing at least a portion of said removed equilibrated blood gases.

14. In a system in accordance with claim 13 wherein said means connected to the exhaust terminal of said catheter for removing said volume of carrier gas including said equilibrated blood gas from said passage to said means for analyzing the blood gases comprises:
an auxilliary source of carrier gas,
pumping means constructed and arranged to induce evacuation and exhaust cycles in said system,
a gas purging valve connected to said pumping means;
a conduit system including a sampling valve having at least two positions for transmission therethrough;
during the evacuation cycle of said system: said sampling valve operable in a first position for connecting the exhaust terminal of said catheter to said pumping means to receive at least a portion of said volume of said carrier gas including said equilibrated blood gas in said sampling valve, and in a second position for connecting said auxilliary carrier source through said sampling valve to said means for analyzing said equilibrated blood gas, whereby said portion is forced into said blood gas analyzing means; and
during the exhaust cycle of said system: said purging valve connectable for purging said pumping means of gas in preparation for the next evacuation cycle.

15. A system in accordance with claim 14 wherein said pumping means comprises automatic vacuum pumping means, and said system comprises detecting means connected adjacent one terminal of said sampling valve and responsive to detect the peak of equilibrated blood gases in said volume of carrier gas passing from said semipermeable membrane member to said sampling valve, and to generate a signal in response to the passage of said peak, and means responsive to said detecting means and actuated by said signal for operating said sampling valve to connect said auxilliary carrier source through said sampling valve to said gas analysis means.

16. A system in accordance with claim 15 wherein the space rate of change of the thermal conductivity of said volume of equilibrated blood gas varies as a function of the distribution of dissolved blood gas therein, and wherein said detecting means is sensitive to the space rate of change of thermal conductivity in said volume.

17. A system in accordance with claim 16 wherein said function is a "bell shaped" curve having a flattened peak, and wherein said defecting means is responsive to a change of slope of said "bell shaped" curve to actuate said sampling valve to introduce a portion of said volume including said equilibrated blood gases represented by the flat portion of said peak into said means for analyzing blood gas.

18. A system in accordance with claim 13 wherein said means for analyzing the blood gases comprises a gas chromatograph.

19. A system in accordance with claim 13 wherein the membrane member comprising said catheter comprises tubular means constructed for insertion percutaneously into the blood vessel in a direction extending along the principal axis thereof and simultaneously providing a continuous gas permeable conduit in contact with the blood of said subject between said input and output terminals,
said input and output terminals both the the proximal end of said tubular means, and
connecting means to said input and output terminals comprising a housing including input and output gas receptacles respectively constructed and arranged for connection in circuit relation to said source of carrier gas at said input receptacle and to said means for analyzing the blood gases at said output receptacle.

20. The combustion in accordance with claim 19 wherein said semipermeable tubular membrane member consists essentially of a polysiloxane polymer.

21. A system in accordance with claim 19 wherein said gas permeable conduit has a substantially uniform cross-section and permeability along its length between said terminals.

22. The combination in accordance with claim 19 wherein said semipermeable tubular membrane member comprises a plurality of lumens interconnected to provide a continuous uniform gas permeable conduit between said input and output terminals having a length in contact with the blood which substantially exceeds the length of said membrane member.

23. The combination in accordance with claim 22 wherein said semipermeable tubular membrane member comprises at least two parallel lumens of substantially uniform cross-section and permeability forming a gas permeable conduit substantially double the length of said tubular membrane member and joined together by connecting means at their distal ends to provide a reversal of gas flow from one to the other, the proximal ends of said lumens respectively connected to said input and output terminals.

24. The combination in accordance with claim 22 wherein each of said lumens has a cross-sectional dimension not exceeding about 0.011 inch and said membrane has an overall cross-sectional dimension not exceeding about 0.028 inch.

25. The combination in accordance with claim 19 wherein said membrane member comprises an external membrane tube coaxial with another tube, said tubes being inter-connected at their distal ends.

* * * * *

UNITED STATES PATENT AND TRADEMARK OFFICE
CERTIFICATE OF CORRECTION

PATENT NO. : 3,983,864
DATED : October 5, 1976
INVENTOR(S) : Ulrich Sielaff, Wilfried R. Peickert and Dale H. Brinkman It is certified that error appears in the above-identified patent and that said Letters Patent are hereby corrected as shown below:

Line 7, "equilibratin" should read -- equilibration --.

Col. 1, line 11, before "vivo" insert -- in --.

Col. 5, line 1, before "tubes" insert -- Connecting --;

line 2, delete "1".

Claim 11, line 2, "to" should read -- of --.

Claim 19, line 9, delete "the" (first occurrence) and substitute -- at --.

Claim 20, line 1, "combustion" should read -- combination --.

Signed and Sealed this

Fourteenth Day of December 1976

[SEAL]

Attest:

RUTH C. MASON
Attesting Officer

C. MARSHALL DANN
Commissioner of Patents and Trademarks